United States Patent [19]

Kapp et al.

[11] 4,256,094

[45] Mar. 17, 1981

[54] ARTERIAL PRESSURE CONTROL SYSTEM

[76] Inventors: John P. Kapp, 455 Bunkers Cove Rd., Panama City, Fla. 32401; James T. Robertson, 628 W. Trezevant, Memphis, Tenn. 38112; Elton M. Tucker, 8 Oxbow Rd., Medfield, Mass. 02052

[21] Appl. No.: 49,419

[22] Filed: Jun. 18, 1979

[51] Int. Cl.³ .................. A61H 9/00; A61B 17/12
[52] U.S. Cl. ............................. 128/24 R; 128/675; 128/DIG. 25; 128/325
[58] Field of Search ............... 128/24 R, 242, 44, 64, 128/673, 674, 675, 677, 325, 346, 326, 327, DIG. 25, 694

[56] References Cited

U.S. PATENT DOCUMENTS

| | | | |
|---|---|---|---|
| 2,690,174 | 9/1954 | Fuchs | 128/64 |
| 3,053,249 | 9/1962 | Smith | 128/64 |
| 3,552,383 | 1/1971 | Krueger | 128/901 |
| 3,592,187 | 7/1971 | Youdin et al. | 128/675 |
| 3,730,186 | 5/1973 | Edmunds, Jr. et al. | 128/325 |
| 4,080,966 | 3/1978 | McWally et al | 128/673 |

OTHER PUBLICATIONS

Folin, Improved . . . Determination of Blood Flow, May 1952, The Review of Scientific Instruments, vol. 23, No. 5, pp. 235-242.

Barnes et al., An Automated Tilting Bed for . . . Control of Blood Pressure, I.E.E.E. Trans. on Bio. Engr., vol. 8ME-21, No. 2, pp. 124-129, Mar. 1974.

Timm et al., Intermittent Occlusion System, IEEE Trans. on Bio. Med. Engr., Oct. 1970, p. 352.

Primary Examiner—Robert W. Michell
Assistant Examiner—Arthur S. Rose
Attorney, Agent, or Firm—Cesari and McKenna

[57] ABSTRACT

An arterial pressure control system comprises an inflatable cuff for encircling the artery and a fluid pump connected to inflate the cuff. The outlet pressure of the pump is controlled by a programmable controller which receives a feedback signal from a pressure sensor contacting the artery downsteam from the cuff. The output of the pressure sensor is compared with a reference value so that the feedback signal to the controller represents the difference between the actual arterial pressure and the desired pressure. The controller thereupon regulates the output pressure of the pump so as to inflate or deflate the cuff as needed to maintain the desired arterial pressure.

7 Claims, 3 Drawing Figures

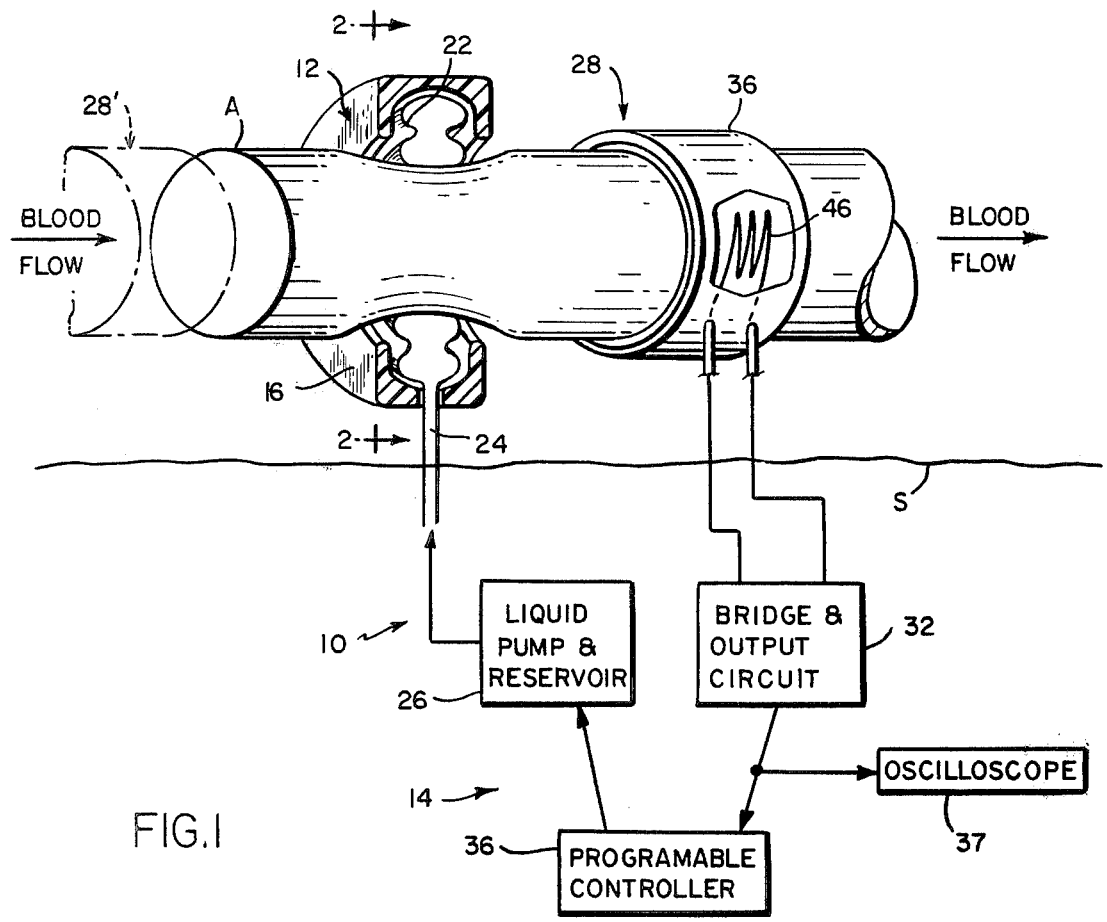
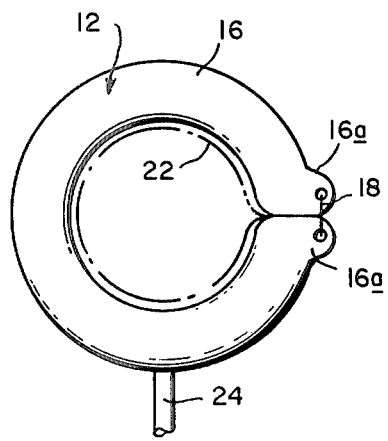
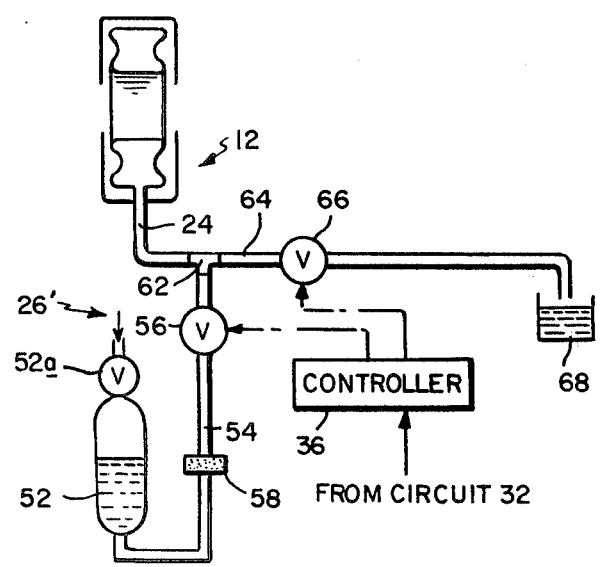

ARTERIAL PRESSURE CONTROL SYSTEM

This invention relates to an arterial pressure control system. It relates more particularly to apparatus for controlledly modifying the arterial pressure to a selected body site and particularly to the head and brain.

BACKGROUND OF THE INVENTION

In some diseases, it is desirable to modify the blood pressure in an artery leading to a particular organ in the body. This may be done, for example, to achieve constriction or reduction of soft organs in acute or chronic indications. It may also be done to relieve arterial pressure to an organ such as the brain following or in anticipation of blood vessel rupture. Currently such arterial occlusion is achieved by engaging a mechanical clamp over the artery wall and manually tightening the clamp until some partial occlusion is achieved.

Quite obviously, the major drawback of this type of occlusion system is that it does not control blood pressure, but simply causes a constant reduction in flow area at the point in the artery where the clamp is installed. Accordingly, if for some reason, the incoming blood pressure increases, there is a commensurate increase in the outgoing pressure leading to the body site which increase may be unacceptably high and dangerous to the patient. Likewise if there is a reduction in the incoming pressure to the artery, there may be an unacceptable further reduction in the outgoing pressure. Such unwanted and unexpected increases or decreases in the blood pressure to the body site served by that artery could cause serious and permanent injury to the patient.

One way to avoid the above problem is to continuously monitor the blood pressure to the body site of interest and manually open or close the clamp to offset observed decreases or increases in blood pressure. However, this necessitates having a nurse constantly in attendance at the patient's bedside and even then the reaction time may not be fast enough to assure reliable control. It would, therefore, be desirable to be able to control arterial pressure automatically.

SUMMARY OF THE INVENTION

Accordingly, the present invention aims to provide an improved system for controlling arterial pressure in selected areas.

Another object of the invention is to provide a system of this type which automatically adjusts arterial pressure to yield a desired predetermined level.

A further object of the invention is to provide an arterial pressure control system which is capable of sensing and modifying to a selected level the maximum or minimum arterial pressure to a selected body site.

Another object is to provide a system of this type which can readily be placed in service in the patient at risk.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, our system includes an inflatable cuff which is positioned and secured around the artery to be partially occluded. The inside surface of the cuff in contact with the artery wall is fitted with an inflatable annular liner. When a fluid such as water is injected through a tube into the cuff, the cuff inflates (grows smaller in inner diameter) and compresses the vessel wall so as to partially occlude it, reducing the downstream blood pressure. On the other hand, withdrawal of liquid from the cuff deflates the cuff allowing the blood vessel to dilate increasing the downstream blood pressure.

Liquid is pumped through the tube into the cuff by means of a small pump which draws fluid from a reservoir. The pump is controlled by a programmable controller which regulates the output volume from the pump and therefore the amount of liquid that is pumped into the artery-occluding cuff.

The arterial pressure downstream from the cuff is measured by a pressure sensor and compared with a selected reference value to provide a control standard for the controller. The controller thereon increases or decreases the pump output volume so as to inflate or deflate the cuff as needed to maintain the arterial pressure substantially equal to the reference value. The downstream arterial pressure is sensed by a pressure sensor in contact with the arterial wall. An increase in arterial pressure applies force to the wall of the artery. Conversely a decrease in arterial pressure reduces force on the wall of the artery. These changes in force on the artery wall cause corresponding changes in the output of the pressure sensor. That output signal is compared with a reference value to provide a difference signal to the controller which thereupon automatically adjusts, via the pump, the inner radius of the occluding cuff to yield the desired downstream arterial pressure level.

The arterial pressure upstream from the occluding cuff may also be measured by a similar pressure sensor whose output may provide additional or redundant patient data.

Thus the present system maintains close control over downstream arterial pressure automatically. The only parts of the system implanted in the patient are the occluding cuff and the sensor. The remaining system components can be located at the patient's bedside. Thus the apparatus is easily adapted to the patient with minimum patient discomfort. The components of the system are relatively simple and of a reliable design for patient safety.

BRIEF DESCRIPTION OF THE DRAWING

For a fuller understanding of the nature and objects of the invention, reference should be had to the following detailed description taken in connection with the accompanying drawings, in which:

FIG. 1 is a diagrammatic view of an arterial pressure control system made in accordance with this invention;

FIG. 2 is a fragmentary elevational view along line 2—2 of FIG. 1, and

FIG. 3 is an alternative hydraulic system not requiring a motor driven pump but operating from a pressurized fluid reservoir.

DESCRIPTION OF THE PREFERRED EMBODIMENT

Turning now to FIG. 1 of the drawing, a control system indicated generally at 10 is arranged to regulate the pressure in an artery A. The system includes an inflatable flexible cuff indicated generally at 12 which is implanted in the patient below his skin line S and engaged around the artery leading to the body site in question. For example, artery A may be the carotid artery leading to the brain.

The inflation cuff 12 is controlled by a control section 14 located outside the patient's body. Control section 14 senses the arterial pressure downstream from cuff 12 and compares that with a desired reference pressure and inflates or deflates cuff 12 as required to maintain the preselected arterial pressure.

As best seen in FIGS. 1 and 2, cuff 12 includes a flexible cut substantially inextensible outer wall 16 which can be fitted around artery A. The opposite ends 16a of the cuff are then secured together by a suture 18 or other similar means so that the wall 16 forms an inextensible annulus all around the artery. An elastic liner 22 forms the inner wall of cuff 12 and that liner engages the artery wall. A tube 24 has one end communicating with the space between the cuff outer wall 16 and liner 22. Tube 24 extends out through the patient's skin line S to the outlet of a pump 26 in section 14. The pump inlet on the other hand is connected to a suitable fluid reservoir.

Referring again to FIG. 1, section 14 also is electrically connected to an arterial pressure sensor shown generally at 28 engaging the artery A downstream from cuff 12. In response to changes in arterial pressure, sensor 28 provides a signal to a bridge and output circuit 32, the signal level being indicative of the pressure level in the artery.

The output of circuit 32 is applied to a programmable controller 36 which compares the signal from output circuit 32 to the preselected value and provides the appropriate instructions to pump 26. Any increase in arterial pressure causes a dilation of the artery A which is sensed by sensor 28 causing a change in resistance in the sensing arm of bridge circuit 32. Thereupon circuit 32 applies a difference signal to controller 36 for comparison with the preselected and preprogrammed value placed into the programmable controller 36. The controller, in turn, signals the pump 26 to increase the volume of the cuff as needed to inflate cuff 12 by the amount necessary to yield an arterial pressure equal to the preselected value. Conversely, if there is a decrease in the downstream arterial pressure, this is also sensed by sensor 28 so that the feedback signal from circuit 32 to the controller causes the controller to reduce the volume of the cuff (reducing the cuff occlusion) as needed to allow the arterial pressure to rise to the preselected reference pressure.

Thus pressure sensor 28 monitors the blood pressure in artery A on a continuous basis so that the constriction produced by cuff 12 on the artery is varied as required to maintain the arterial pressure at the preselected value regardless of pressure increases or decreases upstream from the pressure cuff. Also, if desired the output of the circuit 32 can be applied to an oscilloscope 37 or chart recorder thereby permitting direct observation of the pressure fluctuations in artery A as a function of time.

If desired, a similar sensor shown in dotted lines at 28' in FIG. 1 may be positioned upstream from the cuff 12 to provide an indication of the pressure at that point in the artery and thus yield additional patient data.

Although a variety of different types of arrangements for noninvasive pressure measurement may be used, the sensor and bridge and output circuit described in U.S. Pat. No. 3,149,492 have been found to be suitable. (While it is recognized that invasive pressure measurements could be made, they would compromise the sterility of the flowing blood system, represent a potential point for significant blood loss should leakage occur at the point of vessel entry and increase the risk of thrombosis. The system described is comprised of a cuff 28 that may be engaged around artery A downstream from the cuff 12. A strain gauge 46 mounted in the cuff is connected in a bridge circuit 32 of the type described in the aforesaid patent. An increase in force on the wall of the artery in response to an increase in pressure extends the cuff causing unbalancing of the bridge circuit in one direction of a given magnitude so that a first voltage is applied to the comparing circuit in the controller 36 representing the new arterial pressure. A decrease in arterial pressure allows the cuff to contract so that circuit 32 applies a second voltage to the comparing circuit in controller 36 proportional to the pressure decrease as described in the aforesaid patent. The controller then responds to the output of circuit 32 and instructs the pump appropriately to maintain the arterial pressure equal to the reference pressure.

Instead of utilizing a pump to inflate cuff 12, a pressurized source of liquid may be used for that purpose. An arrangement such as that is shown generally at 26' in FIG. 3. It comprises a fluid-containing pressure vessel 52 having a valved top port 52a by which the vessel 52 can be charged with gas under pressure. A conduit 54 leads from the bottom of vessel 52 to a controllable valve 56. Also a filter 58 may be included in conduit 54 to filter out any particulate matter that might be entrained in the liquid leaving the vessel. The outlet of valve 56 connects to the leg of a T-fitting 62. One arm of fitting 62 is connected to the tube 24 leading to cuff 12. The other arm of the T-fitting connects to a conduit 64 containing a controllable valve 66. The outlet of conduit 64 discharges into a sump 68. The valves 56 and 66 are both actuated by signals from the controller 36 which, as described above, receives pressure-indicating signals from the circuit 32.

During operation of the FIG. 3 apparatus, an increase in the force on the wall of the artery in response to an increase in blood pressure extends the cuff, thereby unbalancing the bridge circuit 32 in one direction so that a first voltage is applied to controller 36 reflecting the new arterial pressure. The controller thereupon responds by controlling valves 56 and 66 to cause an increase in the volume of cuff 12 sufficient to occlude the artery A enough to return the arterial pressure to the reference pressure. Conversely if there is a decrease in arterial pressure, the controller 36 controls valves 56 and 66 so that discharge of liquid to the sump 68 reduces the volume of cuff 12 by the appropriate amount to return the arterial pressure to the reference pressure. Thus, the FIG. 3 system embodiment has all of the advantages of the FIG. 1 arrangement in terms of fast and fine control over blood pressure. It is also easier to control and less expensive to make. Furthermore, the gas pressure in the container 52 can be set so that the maximum fluid discharge pressure from the container will not rupture the cuff 12.

It is also possible to incorporate other types of blood pressure sensors in the present system. For example, instead of utilizing the strain gauge type cuff 38 illustrated in FIGS. 1 and 2, a hydraulic cuff identical to cuff 12 may be utilized. In this event, the tube from such a sensing cuff can be connected to a standard strain gauge diaphragm sensor or Bourdon pressure sensor and the fluid path between the cuff and sensor charged with liquid. Any changes in the blood pressure at the pressure sensing cuff results in a change in the fluid pressure applied to the sensor which thereupon produces an output reflecting that change. The output from the sensor is applied to the controller in the same manner described above to maintain the arterial blood pressure equal to the reference pressure. Also, the blood pressure can be sensed invasively by penetrating the artery with a needle and hydraulically conducting the pressure to a standard diaphragm pressure sensor. Of course, this is not as desirable as sensing the pressure noninvasively for the reasons described above.

Thus the present system provides a very effective means for maintaining a constant blood pressure in an artery or other blood vessel, yet the system is composed of relatively few simple, reliable parts. Further since the cuff 12 and the sensor 28 are the only parts of the system implanted in the body, the patient's arterial pressure can be monitored continuously without any requirement for extensive or complex surgical procedures.

It will thus be seen that the objects set forth above among those made apparent from the preceding description, are efficiently attained, and, since certain changes may be made in the above constructions without departing from the scope of the invention, it is intended that all matter contained in the above description or shown in the accompanying drawing be interpreted as illustrative and not in a limiting sense.

It is also to be understood that the following claims are intended to cover all of the generic and specific features of the invention herein described.

I claim:

1. A blood pressure control system comprising
   A. occluding means for engaging a patient's artery which when increasingly actuated increasingly occludes the artery,
   B. means for actuating the occluding means,
   C. blood pressure sensing means arranged for sensing the blood pressure downstream from the location of the occluding means on the artery,
   D. means establishing a reference pressure,
   E. means for comparing the sensed pressure with the reference pressure to produce a control signal, and
   F. means for controlling said actuating means in response to said control signal so as to increase or decrease the pressure in the artery as necessary to maintain the pressure in the artery at the reference pressure.

2. The system defined in claim 1 wherein said occluding means includes a cuff which comprises:
   A. a flexible, but substantially inextensible outer wall,
   B. a flexible elastomeric liner forming the inner cuff wall, said liner being arranged to contact the wall of the artery encircled by the cuff, and
   C. a fluid inlet leading into the space between the outer wall and the diaphragm.

3. The system defined in claim 2 wherein the actuating means comprises a fluid pump whose inlet is connected to a source of fluid and whose outlet is connected to said cuff inlet.

4. The system defined in claim 1 wherein the actuating means comprises
   A. a pressurizable liquid container,
   B. a flow-controllable liquid inlet path from the container to said cuff inlet,
   C. a flow-controllable liquid outlet path from said cuff inlet to a point of discharge, and
   D. wherein said controlling means controls the flow of liquid along said inlet and outlet paths in response to said control signals so as to maintain the blood pressure in the artery at the reference value.

5. The system defined in claim 1 wherein the pressure sensing means comprises:
   A. a cuff for engaging around the artery,
   B. strain gauge means mounted in the cuff, a resistance value of the strain gauge means changing in response to changes in the shape or dimensions of the cuff.

6. The system defined in claim 1 and further including display means responsive to the output of the sensing means for displaying changes in the arterial pressure.

7. The system defined in claim 1 and further including second pressure sensing means arranged to sense blood pressure in the artery upstream from said occluding means to provide information about upstream arterial pressure.

* * * * *